United States Patent [19]

Goldsmith

[11] Patent Number: 4,566,791
[45] Date of Patent: Jan. 28, 1986

[54] FLUID SAMPLE CELL COMPRISING FRESNEL SECTORS

[75] Inventor: Herbert Goldsmith, Rockville, Md.

[73] Assignee: Pacific Scientific Company, Anaheim, Calif.

[21] Appl. No.: 547,239

[22] Filed: Oct. 31, 1983

[51] Int. Cl.[4] .................... G01N 1/10; G01N 21/00; G01N 15/06

[52] U.S. Cl. .................... 356/246; 250/573; 356/338; 356/410; 356/411

[58] Field of Search ............ 356/246, 338, 410, 411; 250/573

[56] References Cited

U.S. PATENT DOCUMENTS

| | | | |
|---|---|---|---|
| 1,848,874 | 3/1932 | Fitzgerald | 356/432 |
| 2,649,011 | 8/1953 | Black | 88/14 |
| 2,707,900 | 5/1955 | Maresh et al. | 88/14 |
| 3,141,094 | 7/1964 | Strickler | 250/218 |
| 3,164,663 | 1/1965 | Gale | 88/14 |
| 3,501,242 | 3/1970 | De Mey, II et al. | 356/246 |
| 3,524,066 | 8/1970 | Blakkan | 250/218 |
| 3,552,864 | 1/1971 | Shields | 356/246 |
| 3,612,697 | 10/1971 | Nebe | 356/246 X |
| 3,628,872 | 12/1971 | Miranda | 356/201 |
| 3,691,391 | 9/1972 | Kishi | 356/246 X |
| 3,704,951 | 12/1972 | Chupp | 356/75 |
| 3,740,155 | 6/1973 | Keller et al. | 356/180 |
| 3,744,907 | 7/1973 | Whelan | 356/246 X |
| 3,773,424 | 11/1973 | Selgin | 356/181 |
| 3,822,947 | 7/1974 | Aday, Jr. | 356/246 |
| 3,886,364 | 5/1975 | Walker et al. | 250/343 |
| 3,915,570 | 10/1975 | Skala | 250/373 X |
| 4,037,974 | 7/1977 | Fletcher et al. | 356/246 |
| 4,181,441 | 1/1980 | Noller | 250/573 |
| 4,236,076 | 11/1980 | Judge et al. | 250/347 |
| 4,278,887 | 7/1981 | Lipshutz et al. | 250/432 |
| 4,341,471 | 7/1982 | Hogg et al. | 250/574 X |

*Primary Examiner*—John E. Kittle
*Assistant Examiner*—Mukund J. Shah
*Attorney, Agent, or Firm*—Lane and Aitken

[57] ABSTRACT

A fluid sample cell for spectroscopic analysis of a fluid sample includes a fluid-tight compartment for the containment of a fluid sample which is defined by a radiant energy transmissive top, a side wall and a bottom. The bottom comprises a plurality of sectors and a Fresnel disc, whereby radiant energy passing through the compartment impinges upon at least one of the sectors and is specularly reflected from a reflecting surface of the sectors to respective focal points of the sectors.

10 Claims, 6 Drawing Figures

FLUID SAMPLE CELL COMPRISING FRESNEL SECTORS

BACKGROUND OF THE INVENTION

1. Field of the Invention

This invention relates to an improved fluid sample cell for the spectroscopic analysis of a fluid sample.

2. Description of the Prior Art

A number of fluid sample cells are known in the art for the containment of fluid samples during transmission spectroscopic analysis. These cells typically include one opening for the entrance and one opening for the exit of radiant energy, and are positioned in a spectroscopic instrument where a contained sample is irradiated with radiant energy. After passing through the sample, the radiant energy is detected and analyzed to determine the absorptive characteristics of the sample or a constituent thereof.

Because the sample cells of the prior art typically provide the opening for the entry of radiant energy on one side of the cell and the opening for the exit of radiant energy on the other side, the instruments of the prior art usually comprise a radiant energy generating means disposed above the sample cell and a radiant energy detector disposed below the cell. Thus, the length of the instrument must be at least as long as the distance between the generating means and the cell plus the distance between the cell and the detector. This required length of conventional instruments causes them to be bulky and inconvenient.

A spectroscopic instrument that does not necessarily involve the length of other more conventional prior art devices is described in U.S. Pat. No. 4,278,887. There, a fluid sample cell is provided which defines a sample compartment having a radiation energy transmissive top and a bottom composed of a diffuse reflector, such as a diffuse mirror. In operation, a sample in the compartment is irradiated with radiant energy and the radiant energy is diffusely reflected back through the transmissive top to detectors which are located on the same side of the cell as the radiant energy generator.

However a problem with the fluid sample cell described in U.S. Pat. No. 4,278,887 is the relatively low amount of radiant energy that is transmitted to the radiant energy detectors. Because the bottom of the cell consists of a diffuse reflecting surface, radiant energy impinging upon the surface may be reflected at any reflective angle and only a fraction of the radiation traveling in a straight line from the radiation source will arrive at the radiation detector. The relatively low transfer of radiant energy to the detector can compromise the accuracy of the spectroscopic analysis.

Accordingly, there exists a need in the art for a fluid sample cell for use in transmission spectroscopic analysis which is compact and convenient to use, and which will help to avoid inaccuracies of measurement due to inadequate radiant energy transmission to radiation detectors. The present invention satisfies these needs, and fulfills other objectives which will become apparent from the following.

SUMMARY OF THE INVENTION

In accordance with the present invention, a fluid sample cell for the spectroscopic analysis of a fluid sample is provided which includes a fluid-tight compartment for the containment of a fluid sample which is defined by a radiant energy transmissive top, a wall connected to the top, and a bottom connected to the wall. The bottom includes a plurality of sectors of a Fresnel disc, whereby radiant energy passing through the compartment impinges upon the sectors and is specularly reflected from a reflecting surface of said sectors to respective focal points of the sectors.

DESCRIPTION OF THE PREFERRED EMBODIMENTS

The preferred embodiments of the present invention will now be described in detail with reference to the drawings.

Figure 1:
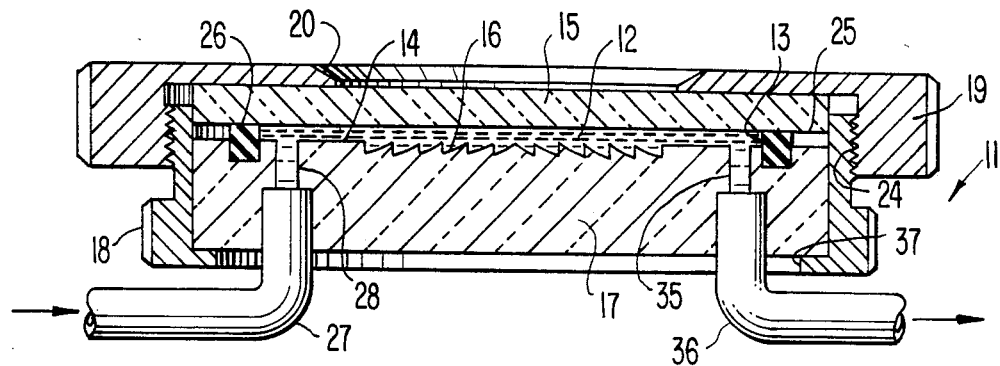
FIG. 1 is a sectional view of a sample cell in accordance with the present invention.

As depicted in FIG. 1, the fluid sample cell 11 can be generally cup shaped and comprises a compartment 12 for the containment of a sample. In the embodiment depicted in these figures, the compartment 12 is defined by an annular side wall 13, a bottom 14 and a radiant energy transmissive top 15. The bottom is provided with a specularly reflecting surface 16 defined by ajoining sectors taken from a Fresnel disc. The specularly reflecting surface is disposed in a block 17 which is in turn contained in a body member 18 having a circular access aperture 37. The transmissive top 15 is partially covered by cover member 19, which defines circular aperture 20. Cover member 19 and body member 18 can be attached by means of complementary threads 24.

Figure 2:
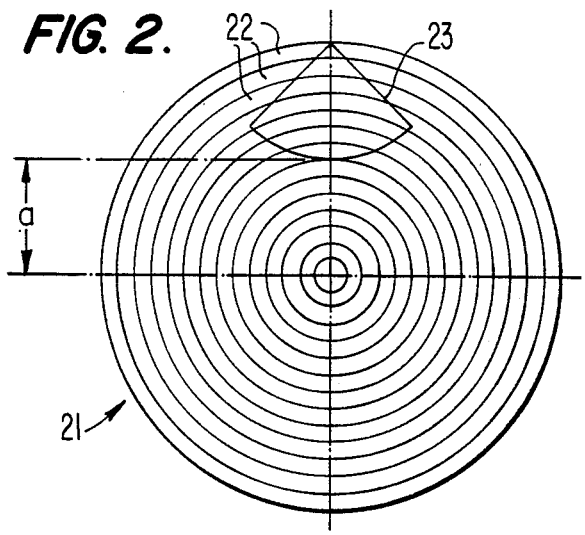
FIG. 2 is a plan view of a Fresnel disc.
Figure 3:
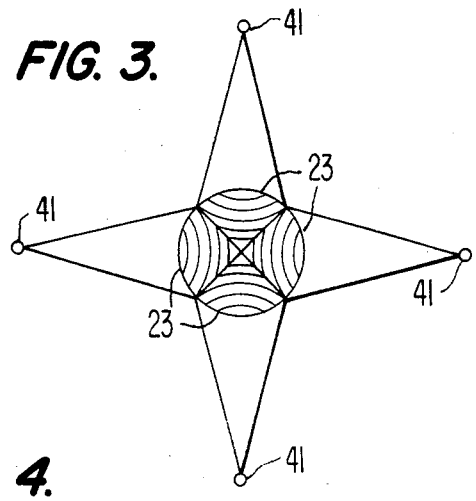
FIG. 3 is a plan view of a reflective surface of the sample cell depicted in FIG. 1.

The nature of the specularly reflecting surface can best be appreciated by reference to FIGS. 2 and 3. In FIG. 2, a Fresnel disc 21 is depicted which has a specularly reflecting surface consisting of a concentric series of concave mirror sections 22. The mirror sections are generally disposed in the same plane, so that the depth of the Fresnel disc is less than the depth of a corresponding concave mirror from which the sections might be derived. However, the optical characteristics of the Fresnel disc is substantially the same as that of a corresponding concave mirror.

The specularly reflective surface 16 of the present invention is produced by piecing together sectors of a Fresnel disc. As depicted in FIGS. 2 and 3, the surface 16 can be comprised of four pie-shaped sectors 23, taken from an outer annular portion of Fresnel disc 21, wherein the apex of the pie shapes are originally disposed on the periphery of the disc, as depicted in FIG. 2. By deriving the sectors from this outer portion, the focal point of each sector is displaced a horizontal distance a from sector 23 so that detector 39 can be positioned at least a like distance b from the path of incident radiant energy, as will be seen in FIG. 4. The sectors depicted in FIG. 3 are identical to one another.

As depicted in FIG. 1, the sectors need not be physically extracted from a Fresnel disc, but can be originally molded in a unitary fashion to simulate the desired surface. In the depicted embodiment, the reflecting surface 16 so formed is connected in a unitary fashion with block 17, but the sectors and block can also be discrete elements, and the block 17 can also be eliminated. Thus, as used in this disclosure, it should be understood that the phrase "sectors of a Fresnel disc" is used broadly to include any surface, regardless of construction, which has specularly reflective properties substantially identical to those of sectors that are actually derived from a Fresnel disc in the manner described above. Also, although four sectors 23 are depicted in FIG. 3, other numbers of ajoining sectors, such as 3, can be employed.

In the embodiment depicted in FIG. 1, cover member 19 is screwed tightly onto body member 18 so that transmissive top 15 is pressed tightly against raised annular mounting ridge 25 and compartment 12 becomes fluid-tight by the compression of O-ring 26. The resting of top 15 on ridge 25 enables the length of the radiant energy path through compartment 12 to be precisely determined.

Means for introducing and purging a fluid sample are depicted in FIG. 1. In this embodiment, a fluid sample can be introduced through inlet conduit 27 and inlet access port 28 to compartment 12. In removing a sample, the sample is passed through exit access port 35 and exit conduit 36. The introduction and purging of samples can be effected through a continuous or a batchwise process.

Figure 4:
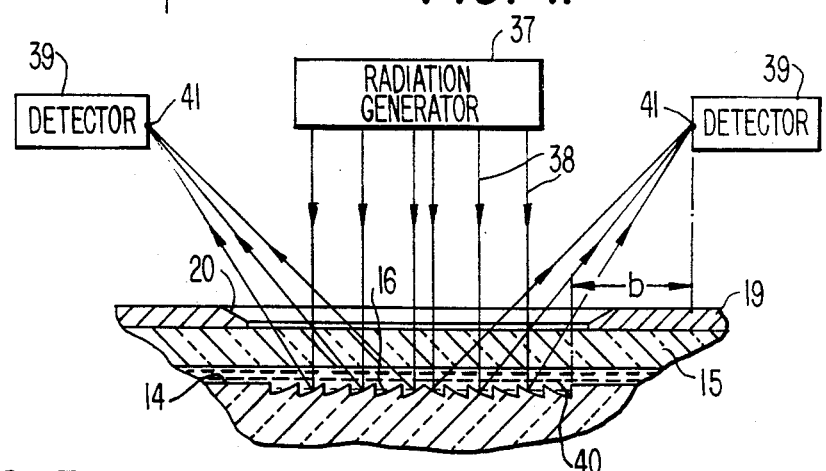
FIG. 4 is a schematic diagram of an apparatus which incorporates the fluid sample cell of FIG. 1.

The apparatus in which the fluid sample cell is to be employed is schematically illustrated in FIG. 4. The apparatus generally consists of a radiation source 37 which is capable of generating radiant energy, indicated by arrows 38, and radiation detectors 39. An apparatus of this general nature is described in greater detail in U.S. Pat. No. 4,236,076.

In operation, a transparent or moderately turbid liquid or gas sample 40 is introduced into compartment 12. In accordance with conventional transmission spectroscopy techniques, radiant energy of a suitable wavelength is selected and generated by radiation source 37, which is positioned to direct the radiant energy in a direction perpendicular to reflecting surface 16. The radiant energy passes through aperture 20, transmissive top 15, and sample 40. As depicted in FIG. 4, and schematically illustrated in FIG. 3, radiant energy impinging upon each sector 23 is specularly reflected to corresponding focal points 41, where the radiant energy is detected by detectors 39 associated with each point. The term "focal point" is used broadly to include a focal area, since the radiant energy that is converged by sectors 23 can be detected at a plurality of points generally indicated by reference numeral 41. A signal processor can receive the output signals of each of the detectors and convert them to a reflectance value, which in turn can be used to determine the concentration of a sample constituent, a property of a sample, etc.

As best seen in FIG. 4, each Fresnel sector 23 has the effect of directing and focusing radiant energy impinging thereon to a respective focal point. The result is much greater radiant energy transfer from the radiant energy source 37 to detectors 39. Substantially all of the radiant energy that is not deflected or absorbed as it passes through sample 40 is transmitted to the detectors. The result is a strong radiant energy input into the detectors which is composed entirely of energy attenutated in proportion to the spectral absorption characteristics of the sample.

Figure 5:
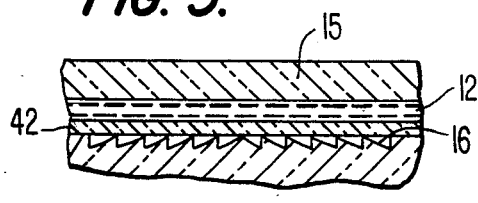
FIG. 5 is a partial sectional view of a fluid sample cell in accordance with an alternative embodiment.
Figure 6:
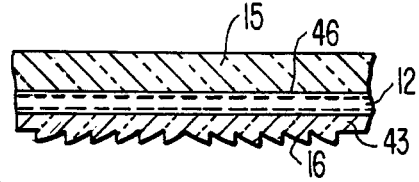
FIG. 6 is a partial sectional view of a fluid sample cell in accordance with another alternative embodiment.

Especially preferred embodiments are depicted in FIGS. 5 and 6. In FIG. 5, sample compartment 12 and reflecting surface 16 are separated by a radiant energy transmissive member 42, such as a transmissive sheet of glass. Although not depicted, the glass could be held in place by any suitable means, such as by bonding the edges of the glass surface to the bottom 14 or side wall 13. It will be appreciated that this arrangement can facilitate maintenance of compartment 12, since the sample does not contact reflecting surface 16 and sample residue cannot, therefore, become lodged in the crevices of the surface. In FIG. 6, maintenance is likewise facilitated by providing a radiant energy transmissive member 43 that has a flat upper surface 46 and which is shaped at its bottom to define and comprise reflecting surface 16.

While the present invention has been described with regard to a number of specific embodiments, it will be readily apparent to those skilled in the art that numerous modifications can be made without departing from the inventive concept of this invention.

What is claimed is:

1. A fluid sample cell for the spectroscopic analysis of a fluid sample comprising a fluid-tight compartment for the containment of a fluid sample, said compartment being defined by a radiant energy transmissive top, a side wall and a bottom, wherein said bottom comprises a plurality of sectors of a Fresnel disc, whereby radiant energy passing through said compartment impinges upon at least one of said sectors and is specularly reflected from a reflecting surface of said sectors to respective focal points of said sectors.

2. The sample cell according to claim 1, wherein said reflecting surface is adjacent to said compartment.

3. The sample cell according to claim 1, wherein said bottom further comprises a radiant energy transmissive member, wherein one surface of said member is adjacent to said compartment and another surface is adjacent to said reflecting surface.

4. The sample cell according to claim 1, wherein said bottom comprises a radiant energy transmissive member having a flat surface which is adjacent to said compartment and a bottom surface which comprises said reflecting surface.

5. The sample cell according to claim 1, wherein there are four of said sectors and four of said respective focal points.

6. The sample cell according to claim 1, wherein there are at least three of said sectors and three of said respective focal points.

7. The sample cell according to claim 1, wherein radiant energy which is reflected to said focal points comprises substantially all of the radiant energy which is transmitted by a radiant energy source and which is not deflected or absorbed by said sample.

8. The sample cell according to claim 1, wherein the incident path of said radiant energy is perpendicular to said reflecting surface.

9. An apparatus for spectroscopic analysis comprising the sample cell according to claim 1, a radiant energy generator disposed above said transmissive top, and a plurality of detectors, a detector being positioned at each of said focal points.

10. The sample cell according to claim 1, wherein said sectors are derived from an outer annular portion of said Fresnel disc.

* * * * *